(12) United States Patent
Ko

(10) Patent No.: US 10,299,860 B2
(45) Date of Patent: May 28, 2019

(54) TREATMENT METHOD USING MULTIPLE ENERGY SOURCES

(71) Applicant: LUTRONIC CORPORATION, Goyang (KR)

(72) Inventor: Kwang Chon Ko, Paju (KR)

(73) Assignee: LUTRONIC CORPORATION, Goyang (KR)

( * ) Notice: Subject to any disclaimer, the term of this patent is extended or adjusted under 35 U.S.C. 154(b) by 162 days.

(21) Appl. No.: 14/778,014

(22) PCT Filed: Mar. 19, 2014

(86) PCT No.: PCT/KR2014/002308
§ 371 (c)(1),
(2) Date: Sep. 17, 2015

(87) PCT Pub. No.: WO2014/148815
PCT Pub. Date: Sep. 25, 2014

(65) Prior Publication Data
US 2016/0278861 A1    Sep. 29, 2016

(30) Foreign Application Priority Data
Mar. 19, 2013   (KR) .................. 10-2013-0029356

(51) Int. Cl.
*A61B 18/00* (2006.01)
*A61B 18/24* (2006.01)
*A61B 18/14* (2006.01)
*A61B 18/22* (2006.01)

(52) U.S. Cl.
CPC .......... *A61B 18/24* (2013.01); *A61B 18/1492* (2013.01); *A61B 2018/00339* (2013.01); *A61B 2018/00994* (2013.01); *A61B 2018/2288* (2013.01)

(58) Field of Classification Search
CPC .................. A61B 18/24; A61B 18/20; A61B 2018/00339; A61B 2018/00994; A61B 2018/2288
USPC .......................................................... 606/14
See application file for complete search history.

(56) References Cited

U.S. PATENT DOCUMENTS

2002/0065541 A1* 5/2002 Fredricks .......... A61B 18/1482
607/96
2003/0225331 A1* 12/2003 Diederich ................ A61N 7/02
600/437

* cited by examiner

*Primary Examiner* — Aaron F Roane

(57) ABSTRACT

The present invention relates to treatment method using multiple energy sources. The treatment method using multiple energy sources, includes: applying a first energy into an inside of an annulus fibrosus; and applying a second energy different from the first energy to an outside of the annulus fibrosus.

11 Claims, 6 Drawing Sheets

TREATMENT METHOD USING MULTIPLE ENERGY SOURCES

BACKGROUND OF THE INVENTION

Field of the Invention

The present invention relates to a method of treating an inside and a surface of an intervertebral disc using multiple energy sources.

Related Art

Since treatment using a laser allows incision, removal, and suture of a bodily tissue without through surgical operation, healing is possible within a short time with a small curing cost. Accordingly, in recent years, the range of curing using the laser is extending to dermatology, an orthopedics, and a plastic surgery as well as a surgery.

The treatment using the laser generally inputs a laser (for example, Nd:YAG laser) toward a bodily tissue. The laser is absorbed in a corresponding bodily tissue so that the corresponding bodily tissue emit heat to use a time period when the corresponding bodily tissue is cut, removed, sewed, and modified.

Meanwhile, various methods of applying energy into an inside of an annulus fibrosus in order to treat the intervertebral disc of the spine have been developed. In the above methods, since an energy supply device is located inside the annulus fibrosus, when the energy supply device is penetrated, the surface of the annulus fibrosus is damaged. However, since an existing method uses only a single energy for internal treatment of the annulus fibrosus, it is difficult to take a suitable action with respect to damage on the surface of the annulus fibrosus.

SUMMARY OF THE INVENTION

The present invention provides a method of treating an inside and a surface of an intervertebral disc using multiple energy sources.

In order to accomplish the above object, in accordance with an aspect of the present invention, there is provided a treatment method using multiple energy sources, the method including: applying a first energy into an inside of an annulus fibrosus; and applying a second energy different from the first energy to an outside of the annulus fibrosus.

The first energy may include a laser, and the applying of the first energy may include: penetrating a delivery means for delivering the first energy into the inside of the annulus fibrosus; and applying the first energy while moving the delivery means into the inside of the annulus fibrosus.

The second energy may be applied to the annulus fibrosus region into which the delivery means is penetrated.

The second energy may include a radio frequency (RF).

The second energy may be applied when the delivery means is separated from the annulus fibrosus after the first energy is applied.

The second energy may include a laser having an energy level different from an energy level of the first energy.

The second energy may be applied through a same delivery means as the delivery means of the first energy, and the second energy may be applied when the delivery means is separated from the annulus fibrosus after the first energy is applied.

In accordance with another embodiment of the present invention, there is provided a treatment method using multiple energy sources, the method including: penetrating a laser delivery means for irradiating a treatment laser into an inside of an annulus fibrosus through a penetration region on a surface of the annulus fibrosus; irradiating the treatment laser into the inside of the annulus fibrosus through the laser delivery means; separating the laser delivery means from the annulus fibrosus after irradiating the treatment laser; and contracting/coagulating the penetration region by applying an energy for contraction/coagulation to the penetration region in the separating of the laser delivery means.

The energy for contraction/coagulation may include a laser and may be applied through a same laser delivery means as the delivery means of the treatment laser.

The energy for contraction/coagulation may include a radio frequency (RF), and an RF delivery means for applying the RF may be integrally formed with the laser delivery means.

Advantageous Effects

In accordance with the present invention, the method of treating an inside and a surface of an intervertebral disc using multiple energy sources is provided.

DESCRIPTION OF EXEMPLARY EMBODIMENTS

Hereinafter, a curing method according to an exemplary embodiment of the present invention will be described with reference to the accompanying drawings. In the following description, a location relationship between constituent elements will be principally described based on drawings. The drawings may be exaggerated, omitted or schematically drawn for the purpose of convenience or clarity. Accordingly, the present invention is not limited thereto. Various variations and modifications are possible in the component parts and/or arrangements of the subject combination arrangement within the scope of the disclosure.

A treatment method according to a first embodiment of the present invention will be described with reference to FIG. 1 to FIG. 3.

An intervertebral disc 100 includes an annulus fibrosus 101 and a nucleus pulposus 102 provided inside the annulus fibrosus. The annulus fibrosus 101 includes a plurality of plates formed by collecting spirally arranged collagenous fiber bundles (collagen fiber bundles). The nucleus pulposus 102 is a hemicolloid organization having gray color where a shape is easily changed and acts as liquid.

The intervertebral disc 100 allows motion between spine bones by connecting the spine bones to each other. The annulus fibrosus 101 supports the spine bone to provide stability and a collagen fiber direction spirally crosses to allow the motion between the spine bones. The nucleus pulposus 102 functions to adsorb shock and to obtain stress balance.

The nucleus pulposus 102 performs a function such as liquid exchange between the intervertebral disc 100 and a capillary tube included in the spine bone. If a parasitic nerve is grown on a surface of the annulus fibrosus 101 due to retrogression and the like, the intervertebral disc 100 causes a pain. If the volume of the annulus fibrosus 101 is increased, peripheral nerves are pushed so that the pain is caused. An object of the present invention is to treat the intervertebral disc 100 diseases.

Figure 1:
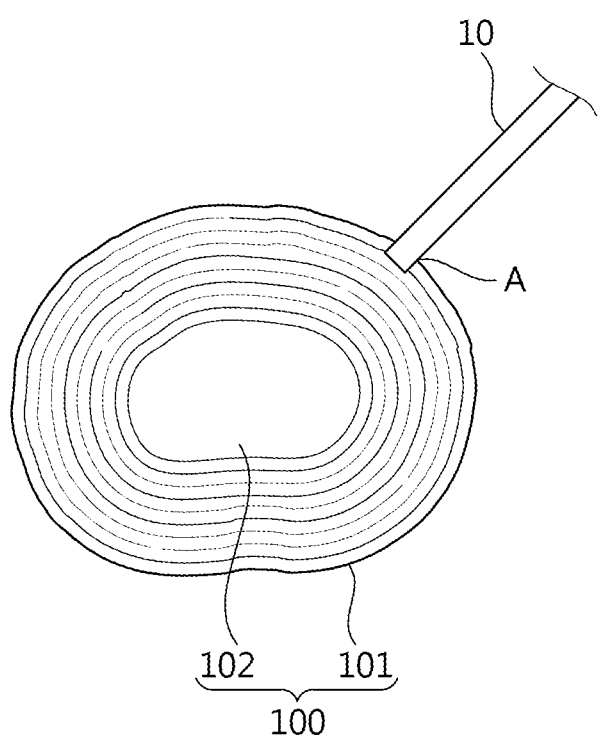
FIG. 1 to FIG. 3 are views illustrating a treatment method according to a first embodiment of the present invention.

First, as shown in FIG. 1, a catheter 10 is penetrated into an inside of the annulus fibrosus 101 through a penetration region A of the annulus fibrosus 101. During the procedure, a trocar (not shown) enters into a shoulder of a patient in a minimally invasive surgery using and then the catheter 10 may enter through a hollow part of the trocar.

The catheter 10 is provided therein with a plurality of channels. The energy and drugs may be supplied through the channels. In addition, treatment regions may be photographed using the channel, illumination necessary for photographing may be provided and water may circulate.

According to the first embodiments, as shown in FIG. 1, an end portion of the catheter 10 is located inside the annulus fibrosus 101.

Figure 2:
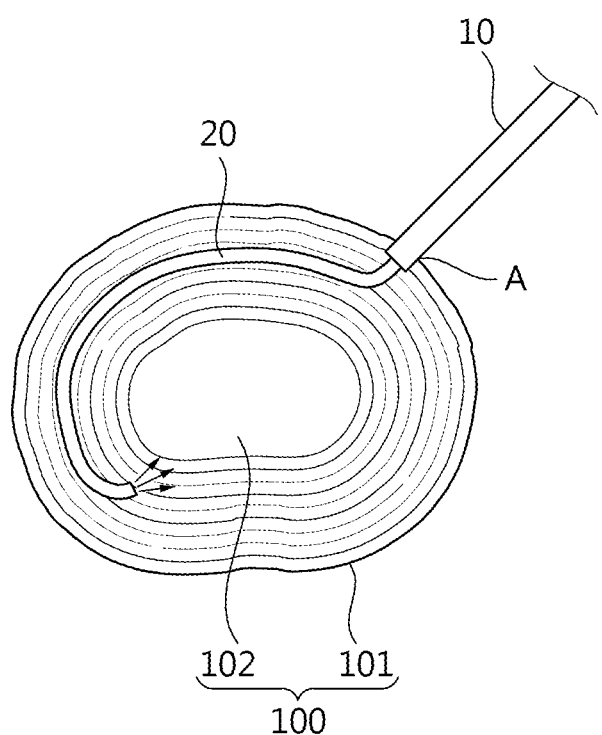
Figure 3:
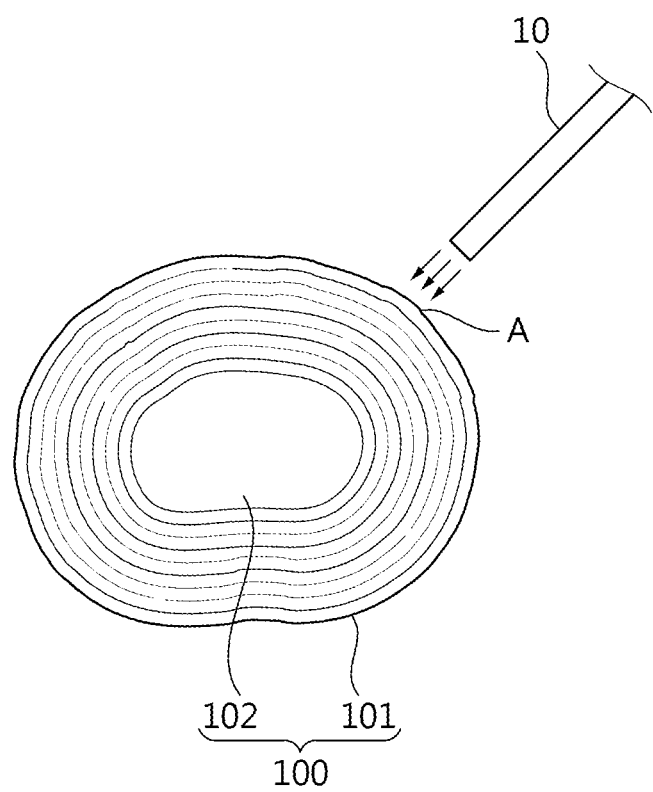

Next, as shown in FIG. 2, an optical fiber 20 enters an inside of the annulus fibrosus 101 and a laser is irradiated. The optical fiber 20 may move between plates of the collagenous fiber bundles (collagen fiber bundles) of the annulus fibrosus 101. When the optical fiber 20 enters and is separated from the inside of the annulus fibrosus 101 of the optical fiber 20, the laser may be irradiated. The irradiation of the laser may be performed during both of the entering procedure and the separation procedure. Both of continuous irradiation or interrupted irradiation is possible.

An organization of the annulus fibrosus 101 is partially ablated by the laser irradiation so that a volume of the annulus fibrosus 101 is reduced. Accordingly, a pain caused by pressing peripheral nerves is attenuated. Further, a temperature of the organization of the annulus fibrosus 101 is increased by laser irradiation so that a temperature of a surface of the annulus fibrosus 101 is increased. Accordingly, a parasitic nerve on the surface of the annulus fibrosus 101 is removed so that the pain is attenuated.

If the laser irradiation with respect to the inside of the annulus fibrosus 101 is completed, the optical fiber 20 exposed to the outside of the catheter 10 is separated from. Next, as shown in FIG. 3, the laser is applied to the penetration region A of a surface of the annulus fibrosus 101 while separating the catheter 10 to an outside of the annulus fibrosus 101. An energy level in the laser applied to the penetration region A may be lower than an energy level of laser for irradiating the inside of the annulus fibrosus 101.

The penetration region A of the annulus fibrosus 101 is damaged due to the penetration of the catheter 10. A problem caused by the damage on the surface of the penetration region A may be solved by applying the laser so that the above part is contracted and/or coagulated. The 'contraction/coagulation' according to the present invention represents 'contraction and/or coagulation' as a treatment aspect generated from the penetration region A on the surface of the annulus fibrosus 101.

The laser for treating the inside of the annulus fibrosus 101 and the laser for coagulating the penetration region A on the surface of the annulus fibrosus 101 may be supplied through a single optical fiber 20. Lasers having different energies may be supplied from different laser supply sources or may be supplied from a single laser supply source.

According to another embodiment, the laser applied to the inside of the annulus fibrosus 101 may be applied to the nucleus pulposus 102 region. According to another embodiment, the laser is applied to the inside of the annulus fibrosus 101 but may be applied to only the nucleus pulposus 102.

Figure 4:
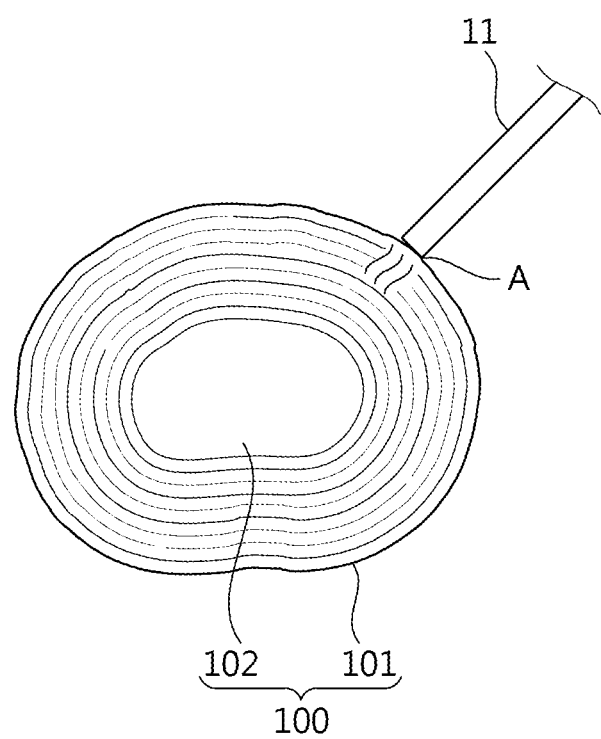
FIG. 4 is a view illustrating a treatment method according to a second embodiment of the present invention.

The second embodiment will be described with reference to FIG. 4. FIG. 4 illustrates a step of applying energy to the penetration region A on the surface of the annulus fibrosus 101 after terminating the laser irradiation into the inside of the annulus fibrosus 101. The second embodiment uses a radio frequency (RF) as the energy applied to the penetration region A.

The laser irradiation to the inside of the annulus fibrosus 101 and applying the RF to the penetration region A on the surface of the annulus fibrosus 101 are performed using the same catheter 11. To this end, an electrode for applying the RF is provided at the catheter 11. The RF may be applied to the penetration region on the surface of the annulus fibrosus 101 in a state that the RF electrode makes contact with the surface of the annulus fibrosus 101.

Figure 5:
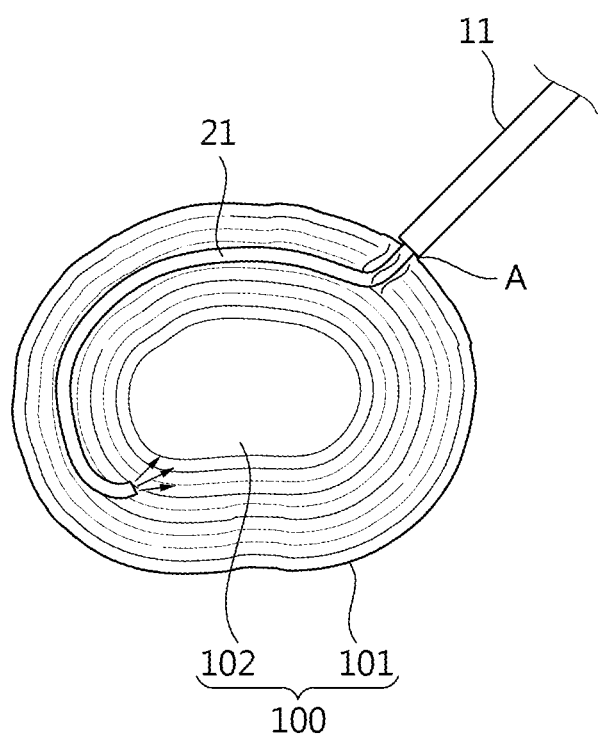
FIG. 5 is a view illustrating a treatment method according to a third embodiment of the present invention.

The third embodiment will be described with reference to FIG. 5. Similar to the second embodiment, the catheter 11 includes both of a device for irradiating the laser and a device for applying the RF. The third embodiment simultaneously performs the laser irradiation to the inside of the annulus fibrosus 101 and applying the RF to the penetration region A on the surface of the annulus fibrosus 101.

According to the third embodiment, after terminating the laser irradiation to the inside of the annulus fibrosus 101, the applying of the RF to the penetration region A on the surface of the annulus fibrosus 101 may be omitted or a time may be reduced. Accordingly, the total time of the surgical operation may be reduced. Since the energy is irradiated to the penetration region A after the penetration region A is damaged, a treatment effect of the penetration region A is excellent.

Figure 6:
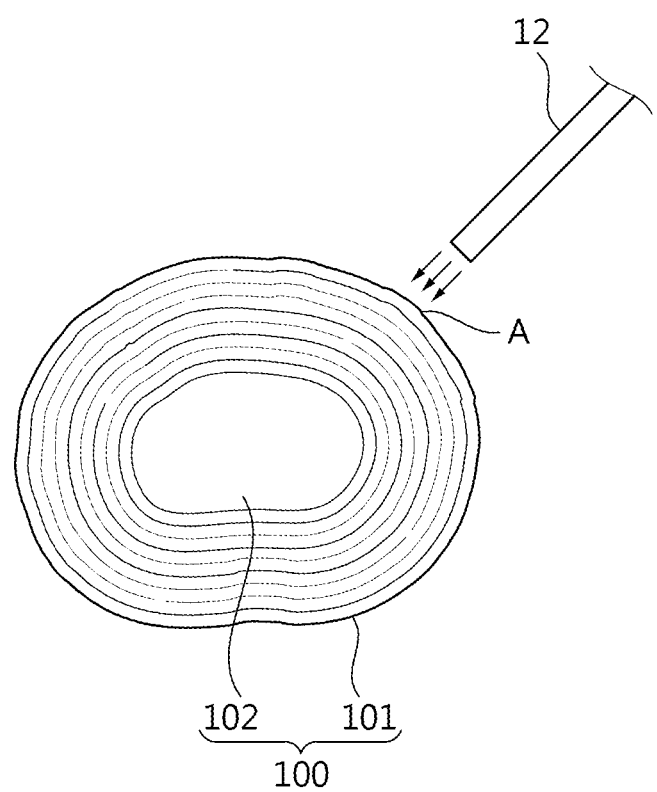
FIG. 6 is a view illustrating a treatment method according to a fourth embodiment of the present invention.

The fourth embodiment will be described with reference to FIG. 6. FIG. 6 illustrates a step of irradiating energy to the penetration region A on a surface of the annulus fibrosus 101 after terminating the laser irradiation to the inside of the annulus fibrosus 101.

The laser is applied to the penetration region A, and the above laser is applied using a separate catheter 12.

The above embodiments are illustrative purpose only for the present invention and an exemplary embodiment of the present invention not limited thereto. Since numerous variations and modifications will become apparent to those skilled in the art once the above disclosure is fully appreciated, the scope and spirit of the invention come within the scope of the appended claims and their equivalents.

What is claimed is:
1. A treatment method using multiple energy sources, the method comprising:
   applying a first energy into an inner layer of an annulus fibrosus by a delivery means inserted through the inner layer of the annulus fibrosus; and
   applying a second energy different from the first energy to a penetration region on an outside surface of the annulus fibrosus,
   wherein a level of the second energy is lower than a level of the first energy,
   wherein a portion of the delivery means is entirely located within the annulus fibrosus when the first energy is applied, the portion of the delivery means protruding from an end of a catheter, and
   wherein the second energy is applied when the delivery means is separated from the annulus fibrosus after the first energy has been applied.
2. The treatment method of claim 1, wherein the delivery means emits a laser, and
   wherein the applying of the first energy comprises:

penetrating through the penetration region on the outside surface of the annulus fibrosus and inserting the delivery means through the inner layer of the annulus fibrosus; and applying the first energy while moving the delivery means in the inner layer of the annulus fibrosus.

3. The treatment method of claim 1, wherein the second energy is applied using a laser that has an energy level lower than an energy level of the first energy.

4. The treatment method of claim 3, wherein the second energy is applied through a same delivery means as the delivery means of the first energy.

5. The treatment method of claim 1, wherein the inner layer of the annulus fibrosus is disposed between a pair of layers of the annulus fibrosus, each of the inner layer and the pair of layers including collagen fiber bundles.

6. The treatment method of claim 1, wherein the delivery means is an optical fiber.

7. The treatment method of claim 1, wherein the delivery means is inserted through the inner layer of the annulus fibrosus by moving the delivery means within the inner layer that is disposed between a pair of layers of the annulus fibrosus, each of the inner layer and the pair of layers including collagen fiber bundles.

8. A treatment method using multiple energy sources, the method comprising:

penetrating a penetration region on an outside surface of an annulus fibrosus and inserting a laser delivery means through an inner layer of the annulus fibrosus;

applying a first energy into the inner layer of the annulus fibrosus through the laser delivery means;

separating the laser delivery means from the annulus fibrosus after applying the first energy; and contracting/coagulating the penetration region by applying a second energy for contraction/coagulation to the penetration region, wherein a level of the second energy is lower than a level of the first energy, wherein a portion of the laser delivery means is entirely located within the annulus fibrosus when the first energy is applied, the portion of the laser delivery means protruding from an end of a catheter, and wherein the second energy is applied when the laser delivery means is separated from the annulus fibrosus after the first energy has been applied.

9. The treatment method of claim 8, wherein the second energy for contraction/coagulation is applied through the laser delivery means.

10. The treatment method of claim 8, wherein the inner layer of the annulus fibrosus is disposed between a pair of layers of the annulus fibrosus, each of the inner layer and the pair of layers including collagen fiber bundles.

11. The treatment method of claim 8, wherein the laser delivery means is an optical fiber.

* * * * *